United States Patent
Geva

(10) Patent No.: US 9,138,144 B2
(45) Date of Patent: Sep. 22, 2015

(54) ADHESIVE BANDAGE AND A METHOD FOR CONTROLLING PATIENT INFORMATION

(75) Inventor: Nir Geva, Nes Ziona (IL)

(73) Assignee: CARD GUARD SCIENTIFIC SURVIVAL LTD., Rehovot (IL)

( * ) Notice: Subject to any disclaimer, the term of this patent is extended or adjusted under 35 U.S.C. 154(b) by 597 days.

(21) Appl. No.: 13/521,223

(22) PCT Filed: Jan. 17, 2011

(86) PCT No.: PCT/IB2011/050193
§ 371 (c)(1),
(2), (4) Date: Jan. 13, 2013

(87) PCT Pub. No.: WO2011/083453
PCT Pub. Date: Jul. 14, 2011

(65) Prior Publication Data
US 2013/0120157 A1 May 16, 2013

Related U.S. Application Data

(60) Provisional application No. 61/293,723, filed on Jan. 11, 2010.

(51) Int. Cl.
*G08B 21/00* (2006.01)
*A61B 5/00* (2006.01)
(Continued)

(52) U.S. Cl.
CPC .............. *A61B 5/0015* (2013.01); *A61B 5/002* (2013.01); *A61B 5/6832* (2013.01); *A61F 13/00051* (2013.01); *A61F 13/02* (2013.01); *A61B 2560/0443* (2013.01)

(58) Field of Classification Search
CPC ............................ A61B 5/0015; A61B 5/6832
USPC ....................................... 340/870.16; 600/483
See application file for complete search history.

(56) References Cited

U.S. PATENT DOCUMENTS 7,625,117 B2    12/2009  Haslett et al.
2003/0206116 A1 *  11/2003  Weiner et al. ............ 340/870.28
2008/0221419 A1    9/2008  Furman
(Continued)

FOREIGN PATENT DOCUMENTS

JP          2002/095642         4/2002

*Primary Examiner* — Mark Rushing
(74) *Attorney, Agent, or Firm* — Reches Patents

(57) ABSTRACT

An adhesive bandage that includes: a thin sheet having an underside provided with a self adhesive; a wireless transmitter; a memory unit, coupled to the wireless transmitter, for storing a patient identifier and for storing patient data that comprises measurement thresholds, vital signs measurements and treatment data; a monitor, coupled to the memory unit, for monitoring vital signs and for generating the vital signs measurements; a wireless receiver for receiving requests to obtain requested patient data; an alert generator, coupled to the memory unit, for generating an alert if a vital sign measurement reached an associated measurement threshold; and a processor, coupled to the wireless transmitter, to the wireless receiver and to the memory unit, for determining whether to transmit, by the wireless transmitter, the requested patient data and the patient identifier, and for determining whether to transmit, by the wireless transmitter, the alert and the patient identifier; and wherein at least one component out of the processor, the alert generator, the wireless transmitter, the memory, the monitor, the memory unit and the wireless receiver is connected to the thin sheet.

17 Claims, 5 Drawing Sheets

(51) Int. Cl.
 *A61F 13/00* (2006.01)
 *A61F 13/02* (2006.01)

(56) References Cited

U.S. PATENT DOCUMENTS

2008/0234598 A1* 9/2008 Snyder et al. ................ 600/545
2008/0281244 A1* 11/2008 Jacobs ........................... 602/41
2008/0287800 A1* 11/2008 Furman ........................ 600/454
2009/0076405 A1* 3/2009 Amurthur et al. ............ 600/529
2009/0209896 A1* 8/2009 Selevan ........................... 602/41
2009/0264712 A1 10/2009 Baldus et al.
2009/0318779 A1* 12/2009 Tran ............................... 600/301
2010/0179389 A1 7/2010 Moroney et al.

* cited by examiner

ADHESIVE BANDAGE AND A METHOD FOR CONTROLLING PATIENT INFORMATION

BACKGROUND OF THE INVENTION

Hospitalizing a patient involves opening a file that holds the patient's personal details. These details will be kept in the hospital's Electronic medical record (EMR). A bracelet with the patient's details written on it is attached to the patient hand and is used for identifying the patient during the hospitalization period.

During the hospitalization, a patient is monitored by a nurse that occasionally enters the room. If a problem occurs, it might not be detected on time and the late detection might lead to a health injury or even death.

In some hospital departments, the patient is constantly monitored by monitoring devices, but this kind of monitoring often involves attaching a wired device to the patient, which is awkward and cause discomfort for the patient. If the patient wants to get up of the bed, he may disconnect the wires and remain unmonitored.

The following US patents publications all being incorporated herein by reference describes a health monitoring device for wireless monitoring vital signs: US Patent application publication serial number 2008/0221419, patent application publication serial number US2008/0249379, patent application publication serial number US2008/0275321, patent application publication serial number US2008/0287800, and patent application publication serial number US2009/0048518.

SUMMARY OF THE INVENTION

According to an embodiment of the invention an adhesive bandage is provided. The adhesive bandage can include: a thin sheet having an underside provided with a self adhesive; a wireless transmitter; a memory unit, coupled to the wireless transmitter, for storing a patient identifier and for storing patient data that comprises measurement thresholds, vital signs measurements and treatment data; a monitor, coupled to the memory unit, for monitoring vital signs and for generating the vital signs measurements; a wireless receiver for receiving requests to obtain requested patient data; an alert generator, coupled to the memory unit, for generating an alert if a vital sign measurement reached an associated measurement threshold; and a processor, coupled to the wireless transmitter, to the wireless receiver and to the memory unit, for determining whether to transmit, by the wireless transmitter, the requested patient data and the patient identifier, and for determining whether to transmit, by the wireless transmitter, the alert and the patient identifier. At least one component out of the processor, the alert generator, the wireless transmitter, the memory, the monitor, the memory unit and the wireless receiver is connected to the thin sheet.

The monitor can include compact sized sensors for measuring the vital signs.

The wireless receiver can be configured to receive additional vital signs measurement from an external device and to forward the additional vital signs measurement to the alert generator.

The processor can be arranged to determine whether to transmit the alert and the patient identifier based on an occurrence of a generation of multiple successive alerts by the alert generator.

The wireless receiver can be configured to receive patient data and wherein the processor can be configured to determine whether to store at least a portion of the patient data in the memory unit.

The wireless receiver can be configured to receive patient data, and wherein the processor can be configured to determine whether to send patient data to an external database via the wireless transmitter.

The processor can be configured to determine whether to retrieve requested patient data from the memory unit or to send a second request to obtain patient data from an external database via the wireless transmitter.

The wireless receiver can be configured to receive a response to a second patient data request from the external database, and wherein the processor can be configured to determine if a patient identifier included in the response correlates to the patient identifier that is stored in the memory unit.

The adhesive bandage can include a power supply.

The wireless receiver and the wireless transmitter can be arranged to use a short range radio frequency transmission.

The wireless receiver and the wireless transmitter can be arranged to use a blue tooth transmission.

The wireless receiver and the wireless transmitter can be arranged to use an infrared transmission.

According to an embodiment of the invention a method is provided. The method the method includes: attaching an adhesive bandage to a patient, wherein the adhesive bandage comprises a thin sheet having an underside provided with a self adhesive, a wireless transmitter, a memory unit, a monitor, a wireless receiver, an alert generator and a processor, wherein at least one component out of the processor, the alert generator, the wireless transmitter, the memory, the monitor, the memory unit and the wireless receiver is connected to the thin sheet; storing a patient identifier and patient data in the memory unit, wherein the patient data comprises measurement thresholds, vital signs measurements and treatment data; monitoring vital signs and generating the vital signs measurements, by the monitor; generating, by the alert generator, an alert if a vital sign measurement reached an associated measurement threshold; determining, by the processor, whether to transmit the alert and the patient identifier; transmitting the alert and the patient identifier if determining, by the processor, to transmit the alert and the patient identifier; receiving, by the wireless receiver, requests to obtain requested patient data;

determining, by the processor, whether to transmit the requested patient data and the patient identifier; and transmitting the requested patient data and the patient identifier if determining to transmit the requested patient data and the patient identifier.

The determining of whether to transmit the alert and the patient identifier can be responsive to an occurrence of a generation of multiple successive alerts.

The method can include receiving the patient data and determining whether to store at least a portion of the patient data in the memory unit.

The method can include receiving the patient data and determining whether to send the patient data to an external database.

The method can include determining whether to retrieve the requested patient data from the memory unit or to send a second request to obtain patient data from an external database.

The method can include receiving a response to a second patient data request from the external database, and determining if a patient identifier indicated in the response correlates to the patient identifier stored in the memory unit.

The method can include monitoring vital signs selected from a list consisting of a body temperature, a heart beat, one lead ECG measurement, O2 saturation and blood pressure.

BRIEF DESCRIPTION OF THE DRAWINGS

The subject matter regarded as the invention is particularly pointed out and to distinctly claimed in the concluding portion of the specification. The invention, however, both as to organization and method of operation, together with objects, features, and advantages thereof, may best be understood by reference to the following detailed description when read with the accompanying drawings in which:

Figure 1:
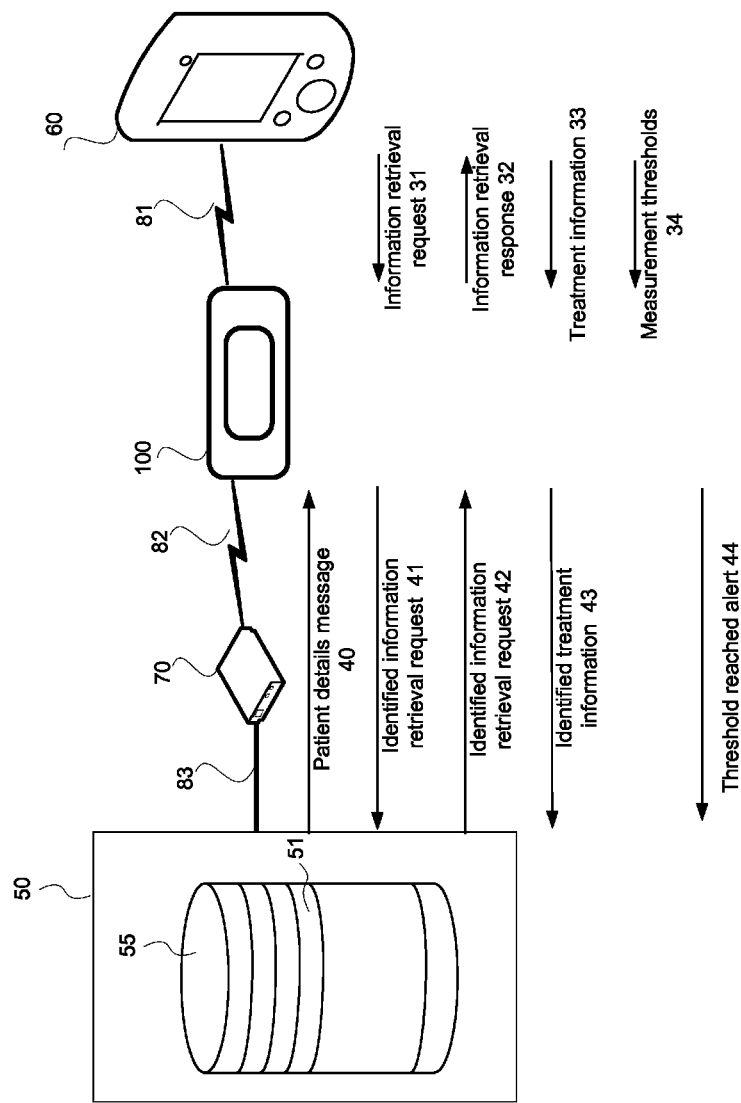
FIG. 1 illustrates the interfaces of an adhesive bandage with external computers, according to an embodiment of the invention.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE PRESENT INVENTION

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

An adhesive bandage for controlling information related to a hospitalized patient is provided. The adhesive bandage is attached to the patient body during a hospitalization period and controls the entire patient's data: personal details including patient's identifier (ID), medical information, a treatment log, test results, drugs prescription and dosage and vital signs monitored measurements.

The adhesive bandage can either store at least part of the patient data in an internal memory unit or it can communicate with a hospital central computer for retrieving patient data from a patient database and for sending patient data that is to be stored in the patient database.

A patient ID that is stored within the internal memory unit of the adhesive bandage is used in each data exchange between the adhesive bandage and the hospital computer, as to identify the patient record in the patient database.

FIG. 1 illustrates adhesive bandage 100 and its external interfaces. Adhesive bandage 100 communicates with an external database 55, e.g. a patient database that stores EMR records of patients, that resides in a hospital computer 50, by utilizing a wireless communication channel 82 through an intermediate dual channel modem 70. Modem 70 communicates with adhesive bandage 100 over a wireless channel 82 on one side and communicates with hospital computer 50 on the other side, using a wired channel 83, e.g. a local area network.

Wireless channel 82 is implemented by using a short range wireless technique e.g. short range RF (Radio Frequency), IR (Infra Red), Blue tooth, or any other short range wireless transmission.

Adhesive bandage 100 also communicates with a handheld device 60 through a wireless channel 81 that implements a similar wireless technique as wireless channel 82. Handheld device 60, e.g. a Personal Digital Assistant (PDA) is used by a medical practitioner that examines the patient and can retrieve patient data controlled by adhesive bandage 100 or update patient data. Retrieving patient data can involve either reading data that is stored within the internal memory unit of adhesive bandage 100 or further request the retrieval of the data from external database 55. Updating patient data, that is requested by handheld device 60 of the medical practitioner, can involve either storing the updated data on the internal memory unit of adhesive bandage 100, sending the updated data to external database 55 or performing both operations. In the latter case, some of the patient data is redundant (resides on both the internal memory unit and external database 55).

During the admission of the patient to the hospital (a process that is usually taken place in the ER), a new patient record 51 is opened in external database 55 that resides on hospital computer 50 and the patient details are recorded in the new patient record. Hospital computer 50 transmits a message: patient details message 40 to adhesive bandage 100, the message contains at least part of the patient details that are stored in patient record 51. Patient details message 40 is received by adhesive bandage 100, through a wireless communication channel 82. The patient details contained in patient details message 40 are stored in the internal memory unit of adhesive bandage 100 and include at least the patient ID but can include further information, such as: known sensitivities to drugs, phone numbers to be called in case of emergency, reason of the hospitalization, drugs that have been taken by the patient before or during the hospitalization, and other personal details.

Treatment data that is gathered during the hospitalization period will be stored in patient record 51 of external database 55, allowing access to any medical practitioner that treats the patient. The treatment data or a portion thereof can be redundantly stored in the internal memory unit of adhesive bandage 100. The treatment data includes: test results, drugs prescription and dosage and any medical procedure executed during the hospitalization.

The medical practitioner uses handheld device 60 for retrieving patient data and updating data. When retrieving patient data, handheld device 60 will send adhesive bandage 100, over wireless channel 81, an information retrieval request 31, requesting to obtain requested patient data. adhesive bandage 100 will check if the requested patient data resides within its internal memory unit. If the requested patient data is found in the internal memory unit, adhesive bandage 100 transmits an information retrieval response 32 to handheld device 60, containing the requested patient data. If the requested patient data is not stored in the internal memory unit, adhesive bandage 100 will read the patient ID that is stored within its internal memory unit, attach it to information retrieval request 31 to provide an identified information retrieval request 41, establish a connection to hospital computer 50 through modem 70 by using wireless channel 82 and send identified information retrieval request 41.

When adhesive bandage 100 receives an identified information retrieval response 42 from hospital computer 50, it determines if a patient identifier indicated in the response correlates to the patient identifier stored in the memory unit and if a correlation is verified, adhesive bandage 100 transmits an information retrieval response 32 to handheld device 60 of the medical practitioner that requested the information.

When the medical practitioner wishes to update treatment data or add new treatment data, he types the new or updated treatment data into his handheld device 60 that in turn sends a message-treatment information 33 to adhesive bandage 100. adhesive bandage 100 attaches the patient ID that is stored in its internal memory unit, to treatment information 33, as to provide a message-identified treatment information 43 and transmits identified treatment information 43 to hospital computer 50 for storing the new or updated treatment information in patient record 51 of external database 55.

Adhesive bandage 100 can periodically monitor the vital signs of the patient and compare vital signs measurements to predefined measurement thresholds. The monitoring can includes reading measurements of the following vital signs: body temperature, heart beat, ECG, O2 saturation (blood oxygen level), blood pressure, or any other vital signs.

Measurement thresholds that are suited for the patient are predetermined by a physician during the patient admission to the hospital, in which case the measurement thresholds are sent from external database 55 to adhesive bandage 100, as part of message-patient details 40. The physician can change the measurement thresholds any time, during the hospitalization, in which case, the new thresholds are entered by the physician using handheld device 60 and are sent to adhesive bandage 100 by a message-measurement thresholds 34. A measurement threshold can include a lower limit of the measurement target, an upper limit or both limits.

Adhesive bandage 100 periodically reads the vital signs within predefined time intervals. The predefined intervals can also be changed during the hospitalization period of the patient. If at least one vital sign measurement drops below the lower limit or rises above the upper limit of the measurement target, adhesive bandage 100 will send a threshold reached alert 44 to hospital computer 50 or to any other computer that handles alerts. Threshold reached alert 44 includes the patient ID, the vital sign which measurement has reached a threshold, the value of the at least one measurement and optionally previously measured values.

The vital sign thresholds can include: required temperature range: 36.5° to 37.5°; O2 saturation: 95%, etc. The measurement thresholds will be stored in the adhesive bandage and will be transmitted to the hospital computer.

Figure 2:
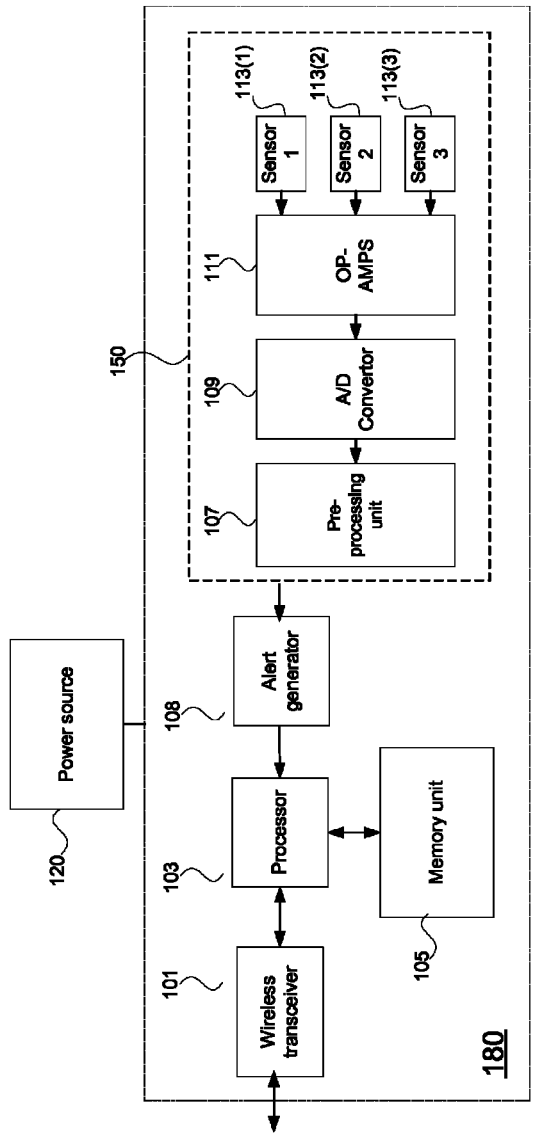
FIG. 2 is a block diagram of the adhesive bandage, according to an embodiment of the invention.
Figure 3:
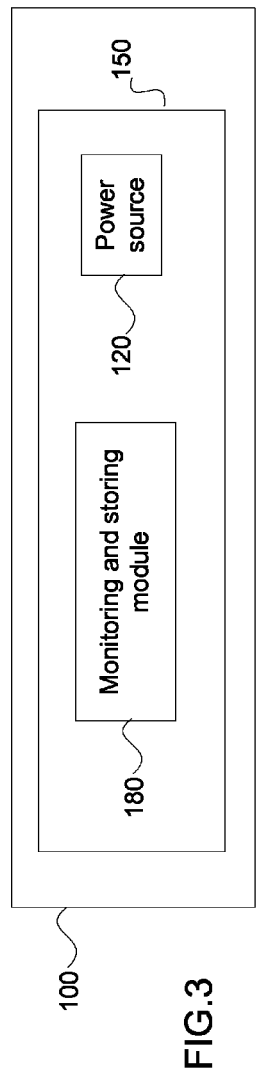
FIG. 3 is a schematic block diagram of the adhesive bandage, according to an embodiment of the invention.

FIG. 2 is a block diagram that illustrates a monitoring and storing module 180 of adhesive bandage 100. Monitoring and storing module 180 is the principal module of adhesive bandage 100 and includes: (i) a monitor 150 for reading vital signs of a patient. Monitor 150 includes compact sized sensors, collectively denoted 113.

Three compact sized sensors, 113(1)-113(3), are illustrated in FIG. 2, but any other amount of sensors can be implemented. Sensors 113 can read any kind of vital sign such as, but not limited to: temperature, heart beat, blood pressure, O2 saturation, 1 lead ECG, etc.

Monitor 150 further includes various components that handles analogue signals including: an operational amplifier 111, an Analog to Digital convertor 109 and a pre-processing unit 107 that includes at least filters; (ii) a wireless transceiver 101 that includes both a wireless transmitter and wireless receiver that can transmit and receive wireless communication and communicates with handheld device 60 and with computer hospital 50 or any other computer; (iii) an alert generator 108 receives vital signs measurements from monitor 150 and generates an alert in case a vital signs measurement reaches an associated measurement threshold; (iv) a processor 103 for determining whether to send threshold reached alert 44 based on the alert generated by the alert generator; controlling wireless transceiver 101 and internal storage 105; and handling all the communication messages between adhesive bandage 100 and hospital computer 50 and all the communication messages between adhesive bandage 100 and handheld device 60 or any other computer; and (v) memory unit 105 for storing: patient identifier, patient data, treatment data, measurement thresholds and optionally vital signs measurement that were read in at least one previous monitoring cycle.

Wireless transceiver 101 can receive vital signs measurement from an external device and forward the vital signs measurement to the alert generator. E.g., the blood pressure or ECG can be wirelessly transmitted by the external device and received by wireless transceiver 101 of adhesive bandage 100.

Figure 4:
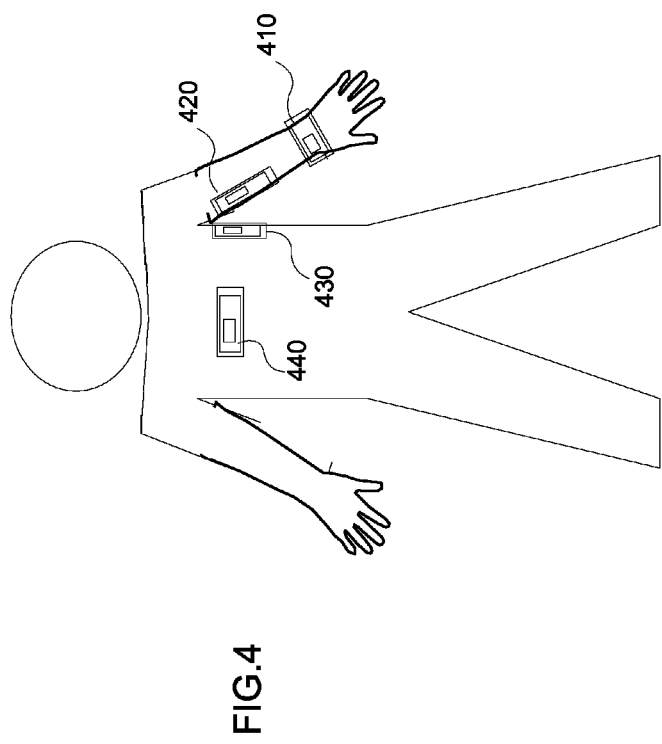
FIG. 4 illustrates the adhesive bandage attached to a human body, according to an embodiment of the invention.

Adhesive bandage 100 is personal and intended for a single use. FIG. 4 illustrates adhesive bandage 100 that includes monitoring and storing module 180 that is attached to a sticky strip 150, wherein sticky strip 150 is adapted to be attached to a body of a patient. Sticky strip 150 is a thin sheet having an underside provided with a self adhesive. Since sticky strip 150 might irritate the skin and since it can loose its sticking ability, there might be a need for replacing sticky strip 150. Monitoring and storing module 180 can be detached from sticky strip 150 and re-attached to a new sticky strip. Sticky strip 150 can hold a power source 120, so it can be replace each time sticky strip 150 is replaced.

According to an embodiment of the invention, adhesive bandage 100 contains a location tracker element, e.g. a GPS or an RFID, that can track down a patient location in the hospital environment.

FIG. 4 illustrates the various options of attaching adhesive bandage 100 to a patient body. Adhesive bandage 100 can be attached to the wrist 410, an inner part of the arm 420, the armpit 430 or the chest 440.

Figure 5:
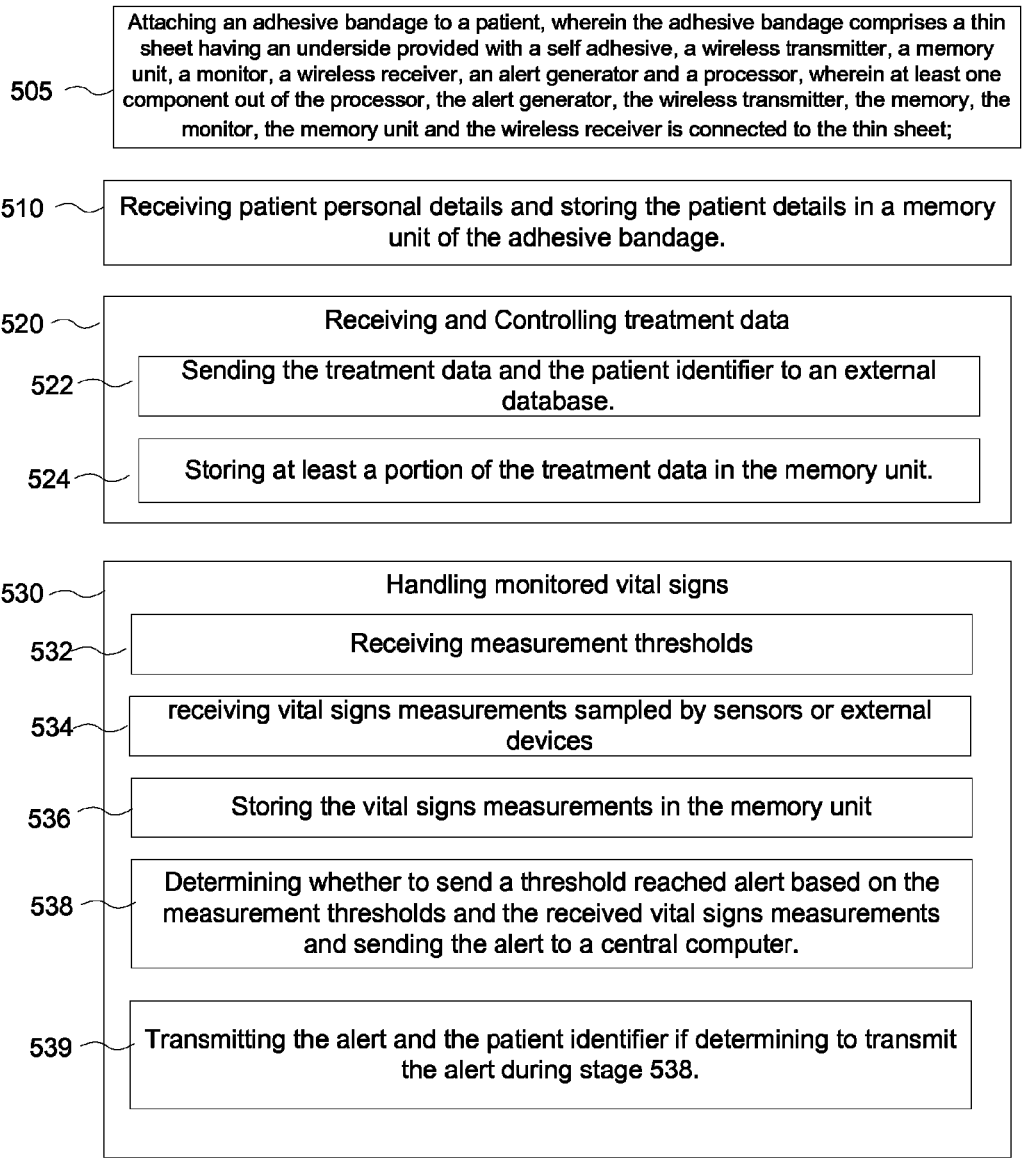
FIG. 5 and FIG. 6 schematically show a flow diagram of a method for controlling a patient data, according to an embodiment of the invention.
Figure 6:
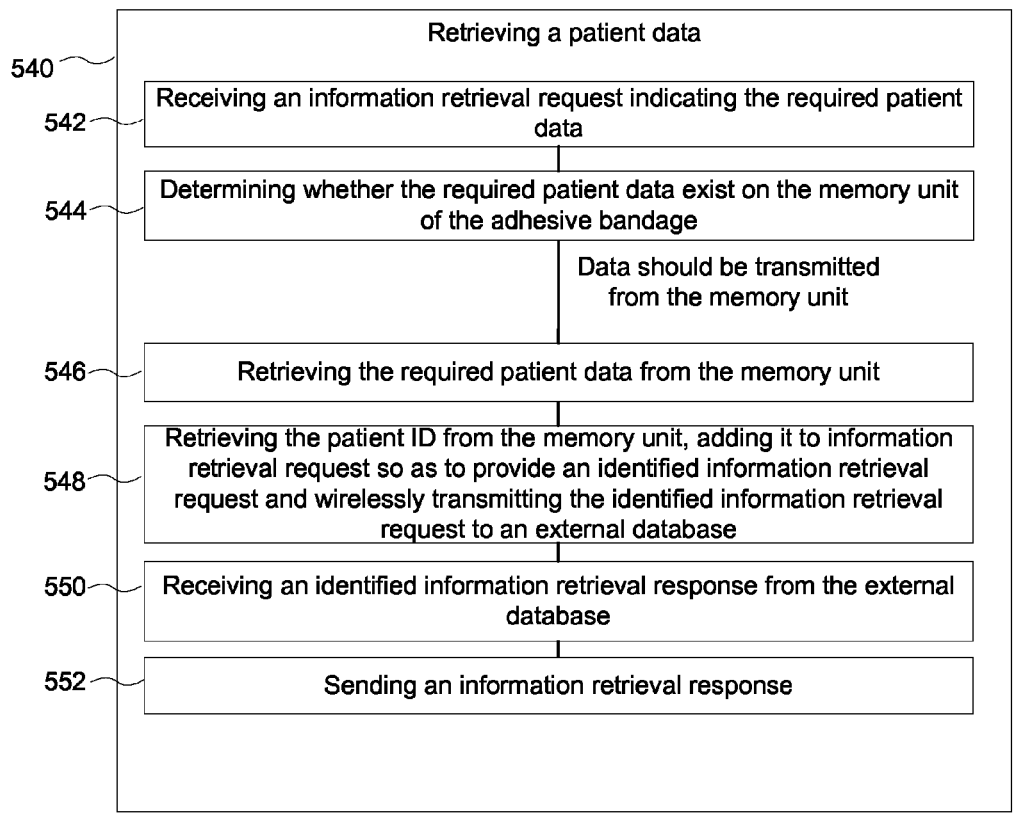

FIG. 5 is a flow diagram of a method 500 for controlling a patient data according to an embodiment of the invention.

Method 500 starts with stage 505 of attaching an adhesive bandage to a patient, wherein the adhesive bandage comprises a thin sheet having an underside provided with a self adhesive, a wireless transmitter, a memory unit, a monitor, a wireless receiver, an alert generator and a processor, wherein at least one component out of the processor, the alert generator, the wireless transmitter, the memory, the monitor, the memory unit and the wireless receiver is connected to the thin sheet.

Stage 505 is followed by stage 510 of receiving patient details and storing the patient details in the memory unit of the adhesive bandage. This stage is taking place upon a patient admission to the hospital. The patient details are received from an external database that may hold a record for each patient during a hospitalization period. The patient details include at least a patient identifier (ID) and may include other personal details, phone numbers to be called in case of emergency, known sensitivities to drugs, reason of the hospitalization, drugs that have been taken by the patient before the hospitalization and so on. The patient details may further include predetermined measurement thresholds of vital signs and time intervals for monitoring the vital signs. Stage 510 may be repeated later on for updating patient details, such as updating the measurement thresholds.

Method 500 further includes stages 520, 530 and 540.

Stage 520 of receiving and controlling treatment data includes stage 522 of sending the treatment data and the patient identifier to an external database, such as the hospital patient database. Stage 522 includes reading the patient identifier from the memory unit of the adhesive bandage. The treatment data may include drugs prescription and dosage or any other treatment orders and medical procedures.

Stage 520 optionally includes stage 524 of storing at least a portion of the treatment data in the memory unit.

Method 500 may include stage 530 of handling monitored vital signs. Stage 530 starts with stage 532 of receiving measurement thresholds. The receiving of measurement thresholds can be a part of stage 510 that is taking place upon a patient admission to the hospital, in which case the measurement thresholds can be part of the patient details that are received in stage 510. Alternatively or additionally, the receiving of measurement thresholds can take place at any time during the hospitalization period, i.e. the physician can change the initial values of the measurement thresholds that were determined in stage 510.

Stage 530 further includes stage 534 of receiving vital signs measurements sampled by sensors or external devices. The receiving of vital signs measurements can include reading the measurements from sensors that are included in adhesive bandage 100. Such sensors are capable of sensing body temperature, heart beat, 1 lead ECG, O2 saturation, blood pressure, or any other vital sign. Alternatively, the receiving of vital signs measurements can include receiving the measurements from external devices, e.g. a sphygmomanometer, that communicates with wireless transceiver 101.

Optionally, stage 530 includes stage 536 of storing the vital signs measurements in the memory unit. The stored vital signs measurements can be used for later retrieval or for sending a threshold reached alert that is based on several measurements, thus avoiding sending an alert upon every irregular measurement.

Stage 530 includes stage 538 of determining whether to send a threshold reached alert based on the measurement thresholds and at least one vital sign measurements and sending the alert to a central computer. Each measurement threshold includes at least one of: a lower limit and an upper limit allowed for a measurement. A measurement threshold can be considered as reached, if the vital sign measurement has been dropped below a lower limit or exceeded an upper limit defined by the measurement threshold. The determination can be conducted according to a single measurement, or according to multiple irregular successive measurements that were stored in the memory unit at stage 536. If the determination is that the threshold is reached, then a threshold reached alert will be sent through the wireless transceiver to an alert center.

Stage 538 can be followed by stage 539 of wirelessly transmitting the threshold reached alert if determining (during stage 538) to transmit the threshold reached alert.

Method 500 includes stage 540 of retrieving a patient data. Stage 540 starts with stage 542 of receiving an information retrieval request indicating the required patient data. The information retrieval request can request any of the following items: patient details such as: patient ID, address, phone number and other personal details, known drug sensitivities, known diseases/symptoms or any other medical history information; treatment information, such as the log of medical procedures applied during the hospitalization; measurements thresholds determined for the patient; and monitored vital signs measurements that were recorded.

The information retrieval request can be sent to the adhesive bandage from a handheld device operated by the physician.

Stage 542 is followed by stage 540 of determining whether the required patient data exists on the memory unit of the adhesive bandage. A patient data can reside on a hospital's central database, on both memory unit and the central database and some data can reside only on the memory unit, for example: recent vital signs measurement are only stored in the memory unit and are not reported to the alert center unless a threshold is reached.

If the determination is that the patient data exists on the memory unit, then stage 542 is followed by stage 546 of retrieving the required patient data from the memory unit.

If the determination is that the patient data do not exist on the memory unit, then it should be retrieved from the external database in which case stage 542 is followed by stage 548 of retrieving the patient ID from the memory unit and add it to information retrieval request so as to provide an identified information retrieval request and send the identified information retrieval request to the external database.

Stage 548 is followed by stage 550 of receiving an identified information retrieval response from the external database.

Stage 550 is followed by stage 552 of sending an information retrieval response to the handheld device. Stage 552 may include verifying that a patient ID indicated in the identified information retrieval response is the same patient ID that is stored in the memory unit.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

What is claimed is:

1. An adhesive bandage, comprising:
a thin sheet having an underside provided with a self adhesive;
a wireless transmitter;
a memory unit, coupled to the wireless transmitter, for storing a patient identifier and for storing patient data that comprises measurement thresholds, vital signs measurements and treatment data;
a monitor, coupled to the memory unit, for monitoring vital signs and for generating the vital signs measurements;
a wireless receiver for receiving requests to obtain requested patient data; an alert generator, coupled to the memory unit, for generating an alert if a vital sign measurement reached an associated measurement threshold; and
a processor, coupled to the wireless transmitter, to the wireless receiver and to the memory unit,
for determining whether to transmit, by the wireless transmitter, the requested patient data and the patient identifier,
for determining whether to transmit, by the wireless transmitter, the alert and the patient identifier; and
for determining whether to retrieve requested patient data from the memory unit or to send a second request to obtain patient data from an external database via the wireless transmitter; and
wherein at least one component out of the processor, the alert generator, the wireless transmitter, the memory, the monitor, the memory unit and the wireless receiver is connected to the thin sheet.

2. The adhesive bandage of claim 1, wherein the monitor comprises compact sized sensors for measuring the vital signs.

3. The adhesive bandage of claim 1, wherein the wireless receiver is configured to receive additional vital signs measurement from an external device and to forward the additional vital signs measurement to the alert generator.

4. The adhesive bandage of claim 1, wherein the processor is arranged to determine whether to transmit the alert and the patient identifier based on an occurrence of a generation of multiple successive alerts by the alert generator.

5. The adhesive bandage of claim 1, wherein the wireless receiver is configured to receive patient data and wherein the processor is configured to determine whether to store at least a portion of the patient data in the memory unit.

6. The adhesive bandage of claim 1, wherein the wireless receiver is configured to receive patient data, and wherein the processor is configured to determine whether to send patient data to an external database via the wireless transmitter.

7. The adhesive bandage of claim 1, wherein the wireless receiver is configured to receive a response to a second patient data request from the external database, and wherein the processor is configured to determine if a patient identifier included in the response correlates to the patient identifier that is stored in the memory unit.

8. The adhesive bandage of claim 1, further comprising a power supply

9. The adhesive bandage of claim 1, wherein the wireless receiver and wireless transmitter are arranged to use a short range radio frequency transmission.

10. The adhesive bandage of claim 1, wherein the wireless receiver and wireless transmitter are arranged to use a blue tooth transmission.

11. The adhesive bandage of claim 1, wherein the wireless receiver and wireless transmitter are arranged to use an infrared transmission.

12. A method for controlling a patient data, the method comprising:
- attaching an adhesive bandage to a patient, wherein the adhesive bandage comprises a thin sheet having an underside provided with a self adhesive, a wireless transmitter, a memory unit, a monitor, a wireless receiver, an alert generator and a processor, wherein at least one component out of the processor, the alert generator, the wireless transmitter, the memory, the monitor, the memory unit and the wireless receiver is connected to the thin sheet;
- storing a patient identifier and patient data in the memory unit, wherein the patient data comprises measurement thresholds, vital signs measurements and treatment data;
- monitoring vital signs and generating the vital signs measurements, by the monitor;
- generating, by the alert generator, an alert if a vital sign measurement reached an associated measurement threshold;
- determining, by the processor, whether to transmit the alert and the patient identifier;
- transmitting the alert and the patient identifier if determining, by the processor, to transmit the alert and the patient identifier;
- receiving, by the wireless receiver, requests to obtain requested patient data;
- determining whether to retrieve the requested patient data from the memory unit or to send a second request to obtain patient data from an external database;
- determining, by the processor, whether to transmit the requested patient data and the patient identifier; and
- transmitting the requested patient data and the patient identifier if determining to transmit the requested patient data and the patient identifier.

13. The method of claim 12, wherein the determining of whether to transmit the alert and the patient identifier is responsive to an occurrence of a generation of multiple successive alerts.

14. The method of claim 12, further comprising receiving the patient data and determining whether to store at least a portion of the patient data in the memory unit.

15. The method of claim 12, further comprising receiving the patient data and determining whether to send the patient data to an external database.

16. The method of claim 12, further comprising receiving a response to a second patient data request from the external database, and determining if a patient identifier indicated in the response correlates to the patient identifier stored in the memory unit.

17. The method of claim 12, comprising monitoring vital signs selected from a list consisting of a body temperature, a heart beat, one lead ECG measurement, O2 saturation and blood pressure.

* * * * *